(12) United States Patent
Kaufholz et al.

(10) Patent No.: US 10,739,431 B2
(45) Date of Patent: Aug. 11, 2020

(54) MAGNETIC RESONANCE EXAMINATION SYSTEM WITH A USER INTERFACE

(71) Applicant: KONINKLIJKE PHILIPS N.V., Eindhoven (NL)

(72) Inventors: Paul Augustinus Peter Kaufholz, Eindhoven (NL); Marius Johannes Van Meel, Eindhoven (NL); Rudolf Theodoor Springorum, Eindhoven (NL); Willem Christiaan Constantijn Furster, Eindhoven (NL); Peter Van Der Meulen, Eindhoven (NL); Vincent Paul Quinten Van Wijk, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 28 days.

(21) Appl. No.: 15/775,405

(22) PCT Filed: Nov. 3, 2016

(86) PCT No.: PCT/EP2016/076470
§ 371 (c)(1),
(2) Date: May 11, 2018

(87) PCT Pub. No.: WO2017/080892
PCT Pub. Date: May 18, 2017

(65) Prior Publication Data
US 2018/0356482 A1 Dec. 13, 2018

(30) Foreign Application Priority Data

Nov. 13, 2015 (IN) .......................... 6114/CHE/2015
Jan. 28, 2016 (EP) .................................... 16153101
Mar. 15, 2016 (EP) .................................... 16160495

(51) Int. Cl.
*G01R 33/54* (2006.01)
*G16H 40/63* (2018.01)
*G16H 50/20* (2018.01)

(52) U.S. Cl.
CPC ......... *G01R 33/546* (2013.01); *G01R 33/543* (2013.01); *G16H 40/63* (2018.01); *G16H 50/20* (2018.01)

(58) Field of Classification Search
CPC .... G01R 33/543; G01R 33/546; G16H 40/63; G16H 50/20
See application file for complete search history.

(56) References Cited

U.S. PATENT DOCUMENTS 6,801,037 B1* 10/2004 Zhang .................... G01R 33/54
324/309
6,904,161 B1   6/2005 Becker et al.
(Continued)

FOREIGN PATENT DOCUMENTS

JP       2004290298 A    10/2004

*Primary Examiner* — Rishi R Patel

(57) ABSTRACT

A magnetic resonance examination system is provided with a graphical user interface and an (software) analysis module. The analysis module is configured to analyze examination information, notably a selected examination protocol, for actions to be taken by the operator, such as connecting auxiliary equipment or radio frequency receiver coils to the magnetic resonance examination system. The analysis module supplies the actions to be taken to the (graphical) user interface at the proper instant before or during carrying-out the examination protocol. In this way the operator is guided and supported in the performance of the selected examination protocol. This improves the efficiency of workflow in performing one or more selected protocols. Preferably, the graphical user interface is provided inside the examination room and may be mounted on the gantry.

12 Claims, 3 Drawing Sheets

(56) References Cited

U.S. PATENT DOCUMENTS

| | | |
|---|---|---|
| 7,715,899 B2 | 5/2010 | Harvey et al. |
| 2006/0058635 A1 | 3/2006 | Lehtonen-Krause |
| 2008/0119715 A1 | 5/2008 | Gonzalez et al. |
| 2009/0175524 A1 | 7/2009 | Kachi et al. |
| 2009/0234218 A1 | 9/2009 | Washburn et al. |
| 2012/0157823 A1 | 6/2012 | Gleich |
| 2013/0275086 A1 | 10/2013 | Grodzki et al. |
| 2015/0320365 A1* | 11/2015 | Schulze ............... G06F 3/0484 600/408 |
| 2015/0362566 A1* | 12/2015 | Haider ................ G01R 33/288 324/309 |
| 2017/0248673 A1* | 8/2017 | Kang .................... A61B 5/055 |

* cited by examiner

MAGNETIC RESONANCE EXAMINATION SYSTEM WITH A USER INTERFACE

CROSS REFERENCE TO RELATED APPLICATIONS

This application is a U.S. national phase application of International Application No. PCT/EP2016/076470, filed on Nov. 3, 2016, which claims the benefit of IN Application Serial No. 6114/CHE/2015 filed Nov. 13, 2015 and EP Application Serial No. 16153101.7 filed on Jan. 28, 2016 and EP Application Serial No. 16160495.4 filed Mar. 15, 2016, each of which is incorporated herein by reference.

FIELD OF THE INVENTION

Magnetic resonance imaging (MRI) methods utilize the interaction between magnetic fields and nuclear spins in order to form two-dimensional or three-dimensional images. Magnetic resonance examination systems are widely used nowadays, notably in the field of medical diagnostics, because for the imaging of soft tissue they are superior to other imaging methods in many respects, do not require ionizing radiation and are usually not invasive.

According to the MRI method in general, the body of the patient to be examined is arranged in a strong, uniform magnetic field $B_0$ whose direction at the same time defines an axis (normally the z-axis) of the co-ordinate system to which the measurement is related. The magnetic field $B_0$ causes different energy levels for the individual nuclear spins in dependence on the magnetic field strength which can be excited (spin resonance) by application of an electromagnetic alternating field (RF field) of defined frequency (so-called Larmor frequency, or MR frequency). From a macroscopic point of view the distribution of the individual nuclear spins produces an overall magnetization which can be deflected out of the state of equilibrium by application of an electromagnetic pulse of appropriate frequency (RF pulse) while the corresponding dynamic magnetic field $B_1$ of this RF pulse extends perpendicular to the z-axis, so that the magnetization performs a precession motion about the z-axis. The precession motion describes a surface of a cone whose angle of aperture is referred to as flip angle. The magnitude of the flip angle is dependent on the strength and the duration of the applied electromagnetic pulse. In the example of a so-called 90° pulse, the magnetization is deflected from the z axis to the transverse plane (flip angle 90°).

After termination of the RF pulse, the magnetization relaxes back to the original state of equilibrium, in which the magnetization in the z-direction is built up again with a first time constant $T_1$ (spin lattice or longitudinal relaxation time), and the magnetization in the direction perpendicular to the z-direction relaxes with a second and shorter time constant $T_2$ (spin-spin or transverse relaxation time). The transverse magnetization and its variation can be detected by means of receiving RF antennae (coil arrays) which are arranged and oriented within an examination volume of the magnetic resonance examination system in such a manner that the variation of the magnetization is measured in the direction perpendicular to the z-axis. The decay of the transverse magnetization is accompanied by dephasing taking place after RF excitation caused by local magnetic field inhomogeneities facilitating a transition from an ordered state with the same signal phase to a state in which all phase angles are uniformly distributed. The dephasing can be compensated by means of a refocusing RF pulse (for example a 180° pulse). This produces an echo signal (spin echo) in the receiving coils.

In order to realize spatial resolution in the subject being imaged, such as a patient to be examined, constant magnetic field gradients extending along the three main axes are superposed on the uniform magnetic field $B_0$, leading to a linear spatial dependency of the spin resonance frequency. The signal picked up in the receiving antennae (coil arrays) then contains components of different frequencies which can be associated with different locations in the body. The signal data obtained via the receiving coils correspond to the spatial frequency domain of the wave-vectors of the magnetic resonance signal and are called k-space data. The k-space data usually include multiple lines acquired of different phase encoding. Each line is digitized by collecting a number of samples. A set of k-space data is converted to an MR image by means of Fourier transformation.

The transverse magnetization dephases also in presence of constant magnetic field gradients. This process can be reversed, similar to the formation of RF induced (spin) echoes, by appropriate gradient reversal forming a so-called gradient echo. However, in case of a gradient echo, effects of main field inhomogeneities, chemical shift and other off-resonances effects are not refocused, in contrast to the RF refocused (spin) echo.

The magnetic resonance examination system's user interface serves to allow the user to issue commands to the magnetic resonance examination system's control unit to select and perform magnetic resonance acquisition sequences to acquire magnetic resonance signals and reconstruct magnetic resonance images from the magnetic resonance signals. These commands may relate to the selection of magnetic resonance acquisition sequences that are associated with particular tissue contrast. The commands may also refer to the geometry planning of the region-of-interest (volumes, slices) from which the magnetic resonance signal are to be acquired. The user interface further serves to provide information on the magnetic resonance examination system's status of operation and to present reconstructed magnetic resonance images to the user.

BACKGROUND OF THE INVENTION

A magnetic resonance imaging system is known from the US-patent application US2009/0234218.

This known magnetic resonance imaging system has a graphical user interface located in the scan room and that displays information relating to the set-up of a patient and of a scan for an MRI exam. The information is manually input by the user.

SUMMARY OF THE INVENTION

An object of the present invention is to provide a magnetic resonance examination system with a user interface that enables a more efficient workflow of imaging a patient to be examined.

This object is achieved by the magnetic resonance examination system comprising:
a user interface and an analysis module,
the user interface being configured to provide examination information representing an MRI examination to the analysis module,
the analysis module being configured to analyse the examination information to derive feedback and optionally guidance to properly conduct the MR examination to the user interface.

An insight of the present invention is that the workflow may be intricate as a large number of preparation steps should be carried-out correctly and in their proper sequential order. The present invention allows to reduce the burden in carrying-out the workflow by having the user interface to provide instructions of steps to be taken on the basis of available information regarding the specific patient to be examined as well as taking into account information regarding the examination protocol that is selected by the user. The examination protocol includes actions to be taken to prepare the patient to be examined, to connect proper radio frequency (RF) coils and to connect auxiliary equipment that is needed to carry out the selected examination protocol. This is achieved by the invention in that the analysis module is configured, typically as a software module, to extract from the selected examination protocol that represents the examination information, the required actions and feedback the need to take these required actions to the user. The analysis module is further configured to achieve that the information is prompted at the proper moment in time to the user. In this way the user is given the opportunity sufficiently early to take the required action, e.g. to connect a radio frequency (RF coil) or auxiliary equipment. The RF coil may be a RF receiver coil or a RF transmit/receiver array with several coils. The timing further is such that the user is supported to carry-out an efficient workflow. The analysis module is further configured to access information on the patient to be examined, from which actions that need to be taken may be derived. For example, the information on the patient may concern the presence of (metallic) implants, which could prompt the requirement to adapt the selected examination protocol to run safely, or select a protocol that involves suppression of metal artifacts, such as a SEMAC or MAVRIC technique. The analysis module may further be configured to correlate patient information, such as presence of a metal implant or pregnancy or other conditions with a selection by the operator of the examination protocol. In the event the selected examination protocol is not fit to be applied, then the analysis module may issue a warning to the user interface. Also there may be special requirements on which local RF receiver coils to be used.

According to an aspect of the invention, the user interface provides information on the steps of the MR examination protocol on the basis of available information, e.g. concerning the patient selected to undergo the MR examination protocol, or details of the MR examination protocol. This information may include actions to be taken in the scope of preparation of the patient for the MR examination. Also the need to connect RF coils or other auxiliary equipment such as for vector electrocardiography or for respiration monitoring. Account may be taken of the collection of radio frequency coils actually available in the clinic at issue. Information may be prompted to the user via the user interface on the proper moment in time to take the action. In this way a smooth workflow to conduct the MR examination protocol is supported. Further, on the basis of information concerning the patient at issue, the user interface may prompt the user to select the MR examination protocol from a particular class of select imaging sequences in the MR examination protocol. For example, the analysis module may derive that suppression of metal artifacts is called for in view of the information of the patient having a metal implant. The via the user interface the user may be instructed to select a proper imaging sequence, e.g. such as SEMAC or MAVRIC. The analysis unit may also autonomously select the proper imaging sequence and inform the user over the user interface of the amended MR examination protocol. The use may also be instructed of positions the patient such that the implant is in a less hazardous position. Further, the user may be instructed to connect RF coils in a proper sequential order, e.g. as the MR examination protocol proceeds.

As the user is guided through the MR examination protocol by the instruction provided over the user interface, the workflow efficiency is improved. Notably this is achieved when the user is prompted proactively, e.g. the connect the selected RF coil or auxiliary equipment so that progress of the workflow is no hampered. The improved efficiency is achieved because the analysis unit determines requirements for steps to be taken in the MR examination protocol and prompts or guides the user to take actions to ensure that the MR examination protocol is properly conducted. Auxiliary equipment to be connected may concern vector electrocardiography equipment that may need to be connected properly in the event that the selected examination protocol includes a cardiac MRI application. Further, the requirement of breath hold in the examination protocol may be recognized by the analysis module and prompt for the connection of a respiration monitor, e.g. formed by a respiratory belt or to employ a navigator technique.

The local RF coils to be connected may be recognized from the examination protocol as well as taken into account the constraint which local RF coils that are actually available for the magnetic resonance examination system in point, or in the hospital. The local RF coil may be a specifically designed RF receiver coil that is adapted to a particular part of the anatomy of the patient to be examined.

Where several local RF coils and auxiliary devices are to be connected, the examination protocol, or workflow efficiency may require that these coils and devices are connected to the magnetic resonance examination system in their proper sequential order. The analysis module may be configured to derive this proper sequential order form the examination protocol and feedback that order to the user over the user interface.

In a preferred embodiment of the invention, the user interface includes a control console remote from the main magnet and a gantry display near the main magnet. Often, the control console is located in the control room, separate from the examination room in which the main magnet is installed. The user interface may further include a gantry display in the examination room. In an example implementation the operator selects the patient and the examination protocol, as laid-out e.g. in an exam card at the console room. The gantry display uses this input as well for the information it needs to show the user interface. In this implementation there is no need for an extra console panel/program in the control room to operate the gantry display, this goes automatic as the workflow runs. The gantry display may be fixedly mounted in the examination room, or may be a portable display, e.g. a tablet computer may be used as the portable display, for a member of staff to carry in the examination room. These control console and the gantry display allow both staff in the control room and in the examination room to receive useful feedback on actions to be taken and to enter data or issue commands to the magnetic resonance examination system's control to selected and perform examination protocols. The operator in the console room may not need feedback from the gantry display. Only the operator(s) in the examination room may need to receive feedback from the gantry display.

In brief, magnetic resonance examination system is disclosed that is provided with a graphical user interface and an (software) analysis module. The analysis module is configured to analyse examination information, notably a selected examination protocol, for actions to be taken by the operator, such as connecting auxiliary equipment or radio frequency receiver coils to the magnetic resonance examination system. The analysis module supplies the actions to be taken to the (graphical) user interface at the proper instant before or during carrying-out the examination protocol. In this way the operator is guided and supported in the performance of the selected examination protocol. This improves the efficiency of workflow in performing one or more selected protocols. Preferably, the graphical user interface is provided inside the examination room and may be mounted on the gantry.

The invention also relates to method of operating a magnetic resonance examination system which achieves a more efficient workflow of imaging a patient to be examined. The invention further relates to a computer program. The computer program of the invention can be provided on a data carrier such as a CD-rom disk or a USB memory stick, or the computer program of the invention can be downloaded from a data network such as the world-wide web. When installed in the computer included in a magnetic resonance imaging system the magnetic resonance imaging system is enabled to operate according to the invention and achieves a more efficient workflow of imaging a patient to be examined.

These and other aspects of the invention will be elucidated with reference to the embodiments described hereinafter and with reference to the accompanying drawing wherein

DETAILED DESCRIPTION OF THE EMBODIMENTS

Figure 1:
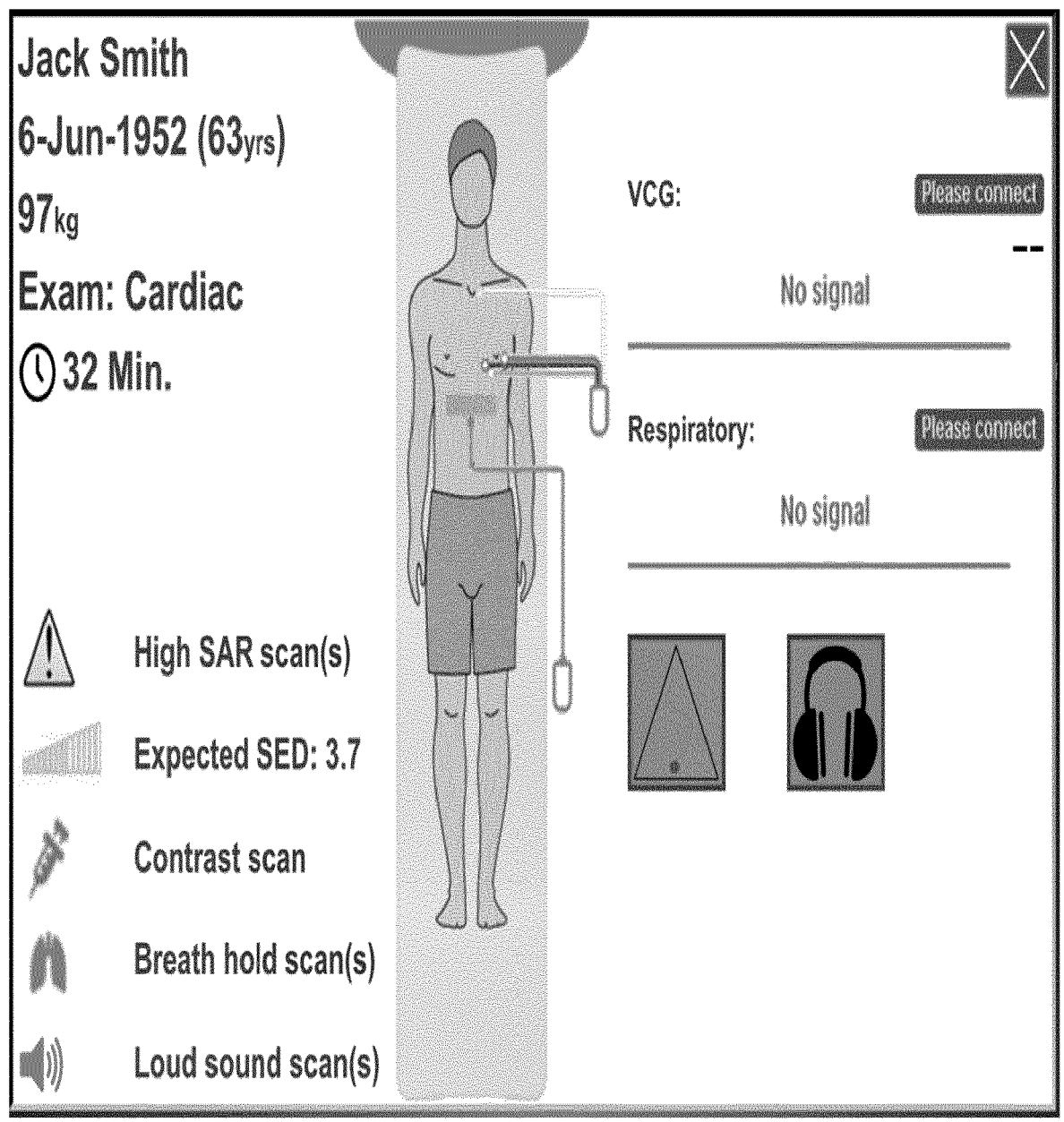
FIGS. 1 and 2 show possible visualizations on a touch screen at the bore for most of the mentioned elements of the invention.
Figure 2:
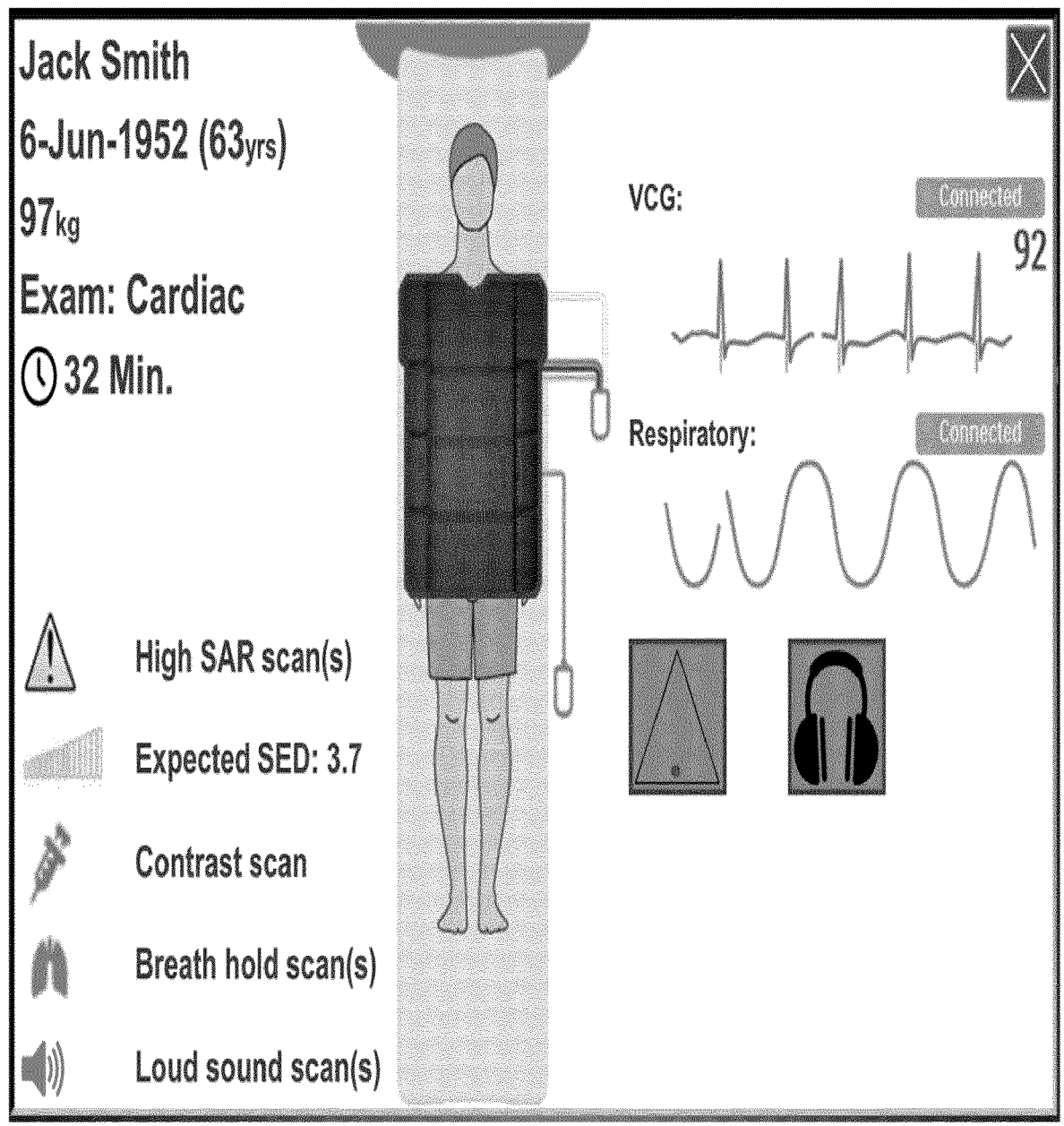

FIGS. 1 and 2 show possible visualizations on a touch screen at the bore for most of the mentioned elements of the invention.

Before an MRI can start the patient has to be prepared and positioned in the MRI scanner. This involves attaching multiple devices like headphones, nurse call, VCG leads, respiratory belt, coil and contrast injector. What devices to attach depends on the characteristics of the examination and the patient.

This invention uses and shows information from both the examination and characteristics of the patient in the exam room. Also, it provides guidance on what devices to attach for this particular exam/patient combination, how they should be attached and in what order. Preparing the patient for an examination takes relative to the whole examination much time. It is critical though that preparation is done well. The first thing to do is verifying that the right patient is coming in. A wrongly prepared patient can lead to bad image quality requiring re-scanning and hence costing time and money. Also, a badly prepared patient can potentially lead to harm. For example, crossing cables can induce currents that might cause burns. Well-positioned headphones/earplugs prevent the patient from hearing damage. The nurse call makes sure help can be called in case of emergency. A patient with an implant may need special pre-cautions while entering the bore. The exam preparation guidance will provide the necessary feedback to the MR Operator to know what is needed, and provide guidance in how and when to perform specific steps in the workflow.

This involves inter alia the following aspects
1. Retrieve relevant information from the examination protocol
2. Specifically, information including:
    Type of examination
    Duration of the examination
    Expected SED
    Presence of high SAR scans
    Patient orientation
    Preferred coil selection
    Presence of breath hold scans
    Contrast agent required
    Sound level of scans
    Vector electro-cardiogram (VCG) required
    Respiratory monitoring required
    The system has knowledge on all characteristics of the exam protocol. This information is passed to the exam room screen UI. Based on the exam type and/or based on the collection of RF coils available in the specific hospital, a (one or more) RF coil(s) is recommended to be connected.
3. Retrieve relevant information from the patient.
4. Specifically, information including:
    Presence of an implant
    Pregnancy status
    Age and gender
    Contra-indications
    Information on the patient known in the system is used on the exam room UI. Information that is required but not yet known can be entered with the exam room UI. If the patient has an implant specific actions may have to be taken while preparing the patient. For example, specifics on forbidden areas for the implant because of high spatial gradient field. This information can be shown on the exam room UI. Also, special coil requirements to safely scan with the implant may overrule the recommended coil for this exam type.
5. Feedback of above information on a display in the exam room near or on the gantry. Feedback on what devices need to be connected. The visualizations above are a possible way to provide relevant feedback.
7. Feedback on the connection status of devices. The system can detect the connection status of multiple devices. This information is used to provide feedback to the MR Operator on device connection and its status. E.g. low battery. A distinction may be made between feedback for a device to see if it is properly connected, and feedback for the signal its receive since a VCG can be connected to the magnetic resonance examination system. If the VCG markers are placed incorrectly the VCG won't get a clear signal, thus showing connected+no signal.
8. Feedback on how to attach specific devices. The orientation of the to-be-connected device, where to connect, and the way that leads are to be positioned are visualized.
9. Guidance on the (preferred) order of attaching devices. When order of connection is important feedback and guidance will be provided sequentially in the expected connection order.
10. Guidance on how and what to instruct the patient. Depending on the patient characteristics or exam type the patient needs to be instructed. E.g. about the exam duration, laying still, performing breath holds. The user or MR Operator is guided in what instructions need to be given on the screen.

11. Ability to input patient or exam specific information at the bore. Some patient or exam specific information may not be known before preparation starts. Possibly this information can be added/changed during preparation using the exam room UI. For example, add patient position on the table, pregnancy status, or change coil selection.

Figure 3:
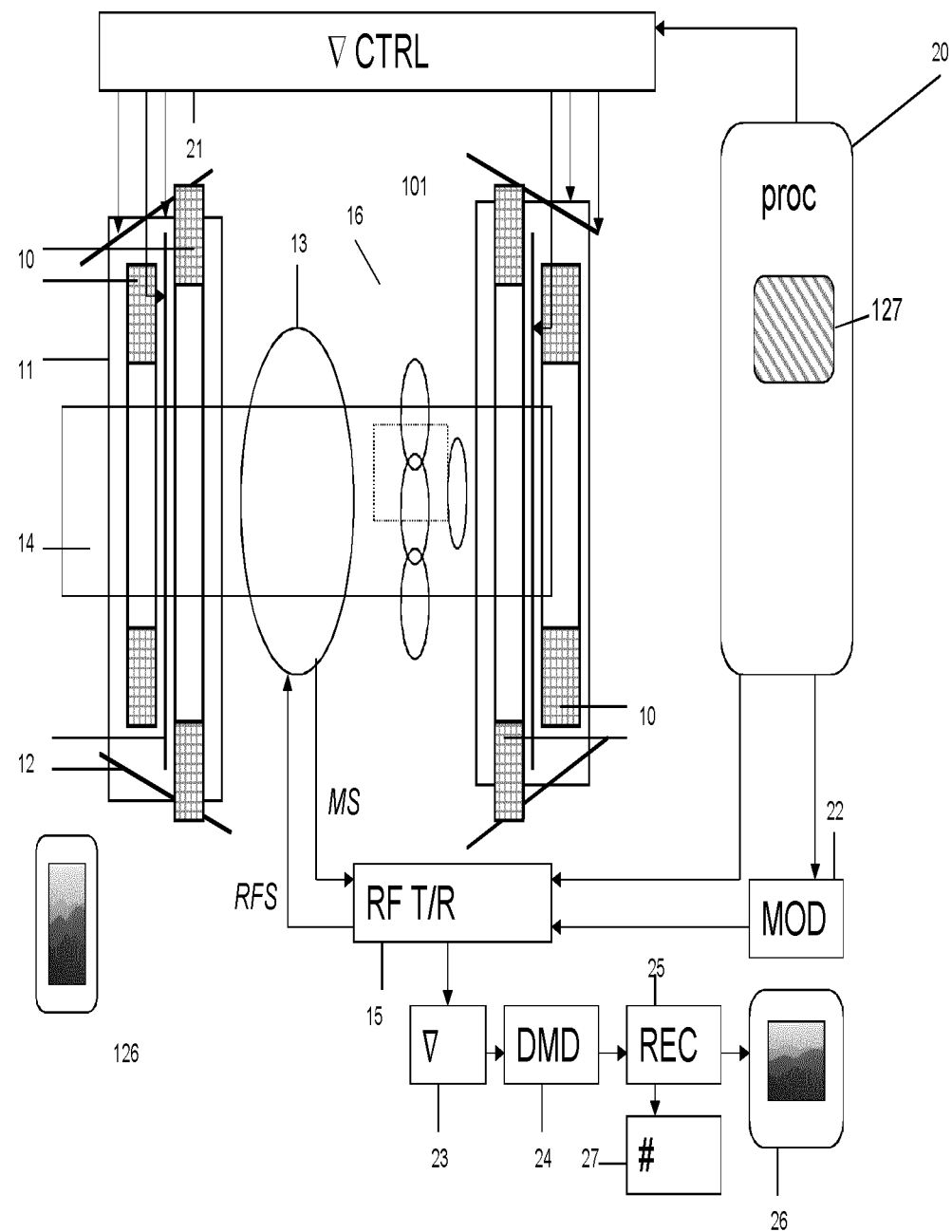
FIG. 3 shows diagrammatically a magnetic resonance imaging system in which the invention is used.

FIG. 3 shows diagrammatically a magnetic resonance imaging system in which the invention is used. The magnetic resonance imaging system includes a main magnet with a set of main coils 10 whereby the steady, uniform magnetic field is generated. The main coils are constructed, for example in such a manner that they form a bore to enclose a tunnel-shaped examination space. The patient to be examined is placed on a patient carrier 14 which is slid into this tunnel-shaped examination space. The magnetic resonance imaging system also includes a number of gradient coils 11, 12 whereby magnetic fields exhibiting spatial variations, notably in the form of temporary gradients in individual directions, are generated so as to be superposed on the uniform magnetic field. The gradient coils 11, 12 are connected to a gradient control 21 which includes one or more gradient amplifier and a controllable power supply unit. The gradient coils 11, 12 are energised by application of an electric current by means of the power supply unit 21; to this end the power supply unit is fitted with electronic gradient amplification circuit that applies the electric current to the gradient coils so as to generate gradient pulses (also termed 'gradient waveforms') of appropriate temporal shape. The strength, direction and duration of the gradients are controlled by control of the power supply unit. The magnetic resonance imaging system also includes transmission and receiving antennae (coils or coil arrays) 13, 16 for generating the RF excitation pulses and for picking up the magnetic resonance signals, respectively. The transmission coil 13 is preferably constructed as a body coil 13 whereby (a part of) the object to be examined can be enclosed. The body coil is usually arranged in the magnetic resonance imaging system in such a manner that the patient 30 to be examined is enclosed by the body coil 13 when he or she is arranged in the magnetic resonance imaging system. The body coil 13 acts as a transmission antenna for the transmission of the RF excitation pulses and RF refocusing pulses. Preferably, the body coil 13 involves a spatially uniform intensity distribution of the transmitted RF pulses (RFS). The same coil or antenna is generally used alternately as the transmission coil and the receiving coil. Typically, a receiving coil includes a multiplicity of elements, each typically forming a single loop. Various geometries of the shape of the loop and the arrangement of various elements are possible. The transmission and receiving coil 13 is connected to an electronic transmission and receiving circuit 15.

It is to be noted that is that there is one (or a few) RF antenna elements that can act as transmit and receive; additionally, typically, the user may choose to employ an application-specific receive antenna that typically is formed as an array of receive-elements. For example, surface coil arrays 16 can be used as receiving and/or transmission coils. Such surface coil arrays have a high sensitivity in a comparatively small volume. The receiving coil is connected to a preamplifier 23. The preamplifier 23 amplifies the RF resonance signal (MS) received by the receiving coil 16 and the amplified RF resonance signal is applied to a demodulator 24. The receiving antennae, such as the surface coil arrays, are connected to a demodulator 24 and the received pre-amplified magnetic resonance signals (MS) are demodulated by means of the demodulator 24. The pre-amplifier 23 and demodulator 24 may be digitally implemented and integrated in the surface coil array. The demodulated magnetic resonance signals (DMS) are applied to a reconstruction unit. The demodulator 24 demodulates the amplified RF resonance signal. The demodulated resonance signal contains the actual information concerning the local spin densities in the part of the object to be imaged. Furthermore, the transmission and receiving circuit 15 is connected to a modulator 22. The modulator 22 and the transmission and receiving circuit 15 activate the transmission coil 13 so as to transmit the RF excitation and refocusing pulses. In particular the surface receive coil arrays 16 are coupled to the transmission and receive circuit by way of a wireless link. Magnetic resonance signal data received by the surface coil arrays 16 are transmitted to the transmission and receiving circuit 15 and control signals (e.g. to tune and detune the surface coils) are sent to the surface coils over the wireless link.

The reconstruction unit derives one or more image signals from the demodulated magnetic resonance signals (DMS), which image signals represent the image information of the imaged part of the object to be examined. The reconstruction unit 25 in practice is constructed preferably as a digital image processing unit 25 which is programmed so as to derive from the demodulated magnetic resonance signals the image signals which represent the image information of the part of the object to be imaged. The signal on the output of the reconstruction is applied to a monitor 26, so that the reconstructed magnetic resonance image can be displayed on the monitor. It is alternatively possible to store the signal from the reconstruction unit 25 in a buffer unit 27 while awaiting further processing or display.

The magnetic resonance imaging system according to the invention is also provided with a control unit 20, for example in the form of a computer which includes a (micro) processor. The control unit 20 controls the execution of the RF excitations and the application of the temporary gradient fields. To this end, the computer program according to the invention is loaded, for example, into the control unit 20 and the reconstruction unit 25.

Further, the magnetic resonance examination system of the invention is provided with a gantry display 126 that is used in the examination room near the magnet of the magnetic resonance examination system. This gantry display 126 may be a mobile device such as a tablet computer. The gantry display may also be mounted on the outside covers of the magnet. The gantry display 126 forms the user interface that provides feedback and optionally guidance from the analysis module 127 to the user. The analysis module 127 may be configured as a software module that is installed in the control unit 20. The analysis module is configured to analyse selected MR examination details, such as listed in an MR examination protocol, including acquisition sequences, for feedback and optionally instructions to the user. The MR examination may be represented by an Examcard and the analysis module is arranged to analyse the Examcard for features in the workflow for which feedback and/or guidance is to be provided to the user.

The invention claimed is:

1. A magnetic resonance (MR) examination system comprising:

a user interface including a control console and a gantry display device configured to be mounted to a magnet of the magnetic resonance system;
a computer processor configured to:
retrieve patient medical information for a patient to be MR imaged, the patient medical information including presence of any implant, pregnancy status, and medical conditions which require specialty local MR cons and/or auxiliary equipment,
retrieve protocol information for a selected MR examination protocol including type of MR examination, patient orientation, and specialty local MR coils and/or other local MR coils and/or auxiliary equipment to be connected to the patient,
determine actions to be taken to prepare the patient to be examined including an order for connecting the specialty local MR coils and/or other local MR coils and/or the auxiliary equipment,
control the gantry display to display the actions to be taken by a clinician adjacent the magnetic resonance system to prepare the patient to be examined to the clinician.

2. The MR examination system according to claim 1, wherein the computer processor is further configured to:
based on the patient medical information and the protocol information, determine whether the selected type of MR examination protocol is appropriate for the patient,
control the gantry display to display a warning if the selected MR examination protocol is inappropriate for the patient.

3. The magnetic resonance examination system according to claim 1, wherein the computer processor is further configured to:
determine local MR coils and auxiliary equipment which are available.

4. The magnetic resonance examination system according to claim 1, wherein the computer processor is further configured to:
determine whether the auxiliary equipment are properly connected to the patient.

5. The magnetic resonance examination system according to claim 1, wherein the computer processor is further configured to:
determine the status of the auxiliary equipment, including if an auxiliary equipment has a low battery.

6. The magnetic resonance examination system according to claim 1, wherein the computer processor is further configured to:
control the gantry display to display instructions for how to attach the auxiliary equipment.

7. The magnetic resonance examination system according to claim 1, wherein the computer processor is further configured to:
control the gantry display to provide instructions to be given to the patient.

8. The magnetic resonance examination system according to claim 1, wherein the control console is disposed remote from a magnetic resonance examination room.

9. The magnetic resonance examination system according to claim 8, wherein the computer processor is further configured to:
deliver guidance information for conducting the MR examination to the control console.

10. A method of operating a magnetic resonance examination system which has a gantry display mounted to a magnet of the magnetic resonance system, the method comprising:
retrieving patient medical information for a patient to be MR imaged, the medical information including presence of any implant, pregnancy status, and medical conditions which require specialty local MR coils and/or auxiliary equipment;
retrieve protocol information for a selected MR examination protocol, including a type of MR examination, patient orientation, and specialty local MR coils and/or other local MR coils and/or auxiliary equipment to be connected to the patient;
determine specialty local MR coils and/or other local MR coils and auxiliary equipment to be connected to the patient;
determine actions to be taken to prepare the patient to be examined including an order for connecting the specialty local MR coils and/or other local MR coils and the auxiliary equipment;
controlling the gantry display to display the actions to be taken to prepare the patient to be examined to the user.

11. A non-transitory computer-readable medium carrying software configured to control a computer processor of a magnetic resonance examination system to perform the method of claim 10.

12. A magnetic resonance examination system including:
a user interface and an analysis module,
the user interface being configured to provide information representing details of successive steps in a selected magnetic resonance imaging examination protocol to the analysis module,
the analysis module being configured to analyze patient medical information and examination protocol information and derive actions and guidance for a clinician to properly conduct the MR examination including:
extracting actions from the selected examination protocol regarding actions to be taken by the clinician,
conveying the actions to be taken to the user interface,
deriving devices to be connected with the patient, and
sending information regarding the devices to be connected to the user interface,
wherein the information includes a status of the devices to be connected and how to connect the devices,
wherein the patient medical information includes presence of any implants, pregnancy status and medical conditions which require specialty local MR coils and/or auxiliary equipment,
wherein the actions include an order for connecting the specialty local MR coils and other local MR coils and/or auxiliary equipment, and
controlling a gantry display to display the actions to be taken by the clinician adjacent the magnetic resonance examination system to prepare the patient for imaging.

* * * * *